United States Patent [19]
Kido et al.

[11] Patent Number: 5,964,901
[45] Date of Patent: Oct. 12, 1999

[54] METHOD FOR DETECTING CLOGGING AND GRANULATION METHOD

[75] Inventors: Kimikazu Kido, Ichikawa; Tetsuzo Honda, Urayasu, both of Japan

[73] Assignee: Toyo Engineering Corporation, Tokyo, Japan

[21] Appl. No.: 08/981,401
[22] PCT Filed: Apr. 8, 1997
[86] PCT No.: PCT/JP97/01198
§ 371 Date: Dec. 16, 1997
§ 102(e) Date: Dec. 16, 1997
[87] PCT Pub. No.: WO97/38789
PCT Pub. Date: Oct. 23, 1997

[30] Foreign Application Priority Data

Apr. 16, 1996 [JP] Japan .................................. 8-094412

[51] Int. Cl.$^6$ .............................. C05B 19/00; C05C 7/02
[52] U.S. Cl. .................................. 23/313 FB; 23/313 R; 422/110; 422/140; 425/222
[58] Field of Search .......................... 23/313 R, 313 FB; 425/222; 422/140, 112, 110; 34/364; 71/64.08

[56] References Cited

U.S. PATENT DOCUMENTS

| | | | |
|---|---|---|---|
| 3,903,333 | 9/1975 | Shirley et al. | 71/64 |
| 4,749,595 | 6/1988 | Honda et al. | 427/213 |
| 5,013,336 | 5/1991 | Kempf et al. | 422/177 |
| 5,108,034 | 4/1992 | Houy et al. | 425/10 |

FOREIGN PATENT DOCUMENTS

| | | |
|---|---|---|
| 3-73525 | 7/1991 | Japan . |
| 7-158837 | 6/1995 | Japan . |

*Primary Examiner*—Gary P. Straub

*Attorney, Agent, or Firm*—Flynn, Thiel, Boutell & Tanis, P.C.

[57] ABSTRACT

There is disclosed a method for detecting clogging of air feed pipes, comprising air feed pipes (15), each having an outlet (13) for jetting air into a granulation section (1), and jetting nozzles (13), each situated at the center of the air outlet of a said air feed pipe for jetting a liquid of a molten raw material (e.g. molten urea), wherein, in jetting the liquid of the molten raw material from the jetting nozzles into the granulation section to carry out granulation, (a) an orifice section (14) is provided at a lower part of each of the air feed pipes (15), a section for taking up orifice rear pressure (16) is provided in each air feed pipe and is located downstream of the orifice section, and a section for taking up orifice forward pressure (17) is provided upstream of the orifice section, and (b) the pressure difference between the orifice forward pressure and the orifice rear pressure is measured, to detect clogging of the air feed pipes based on an abnormality in the pressure difference regarding the air feed pipes. There is also disclosed a granulation method, comprising monitoring the pressure difference by the above method, stopping the feed of a liquid of a molten raw material to the air feed pipe whose pressure difference is abnormal, and compensating the amount corresponding to the stoppage with the remaining function. The detection method is a method capable of detecting accurately a malfunction related to jetting of air in the granulation of urea or the like. Further, the granulation method is a granulation method wherein, accurately, in response to the occurrence of a malfunction related to the jetting of air, the feed of a raw material liquid to the malfunctioned section is stopped, and the raw material liquid to be fed to the jet nozzles having other normal air outlets is suitably increased, thereby allowing continuous operation, with the productivity before the occurrence of the malfunction kept.

8 Claims, 4 Drawing Sheets

F I G. 1
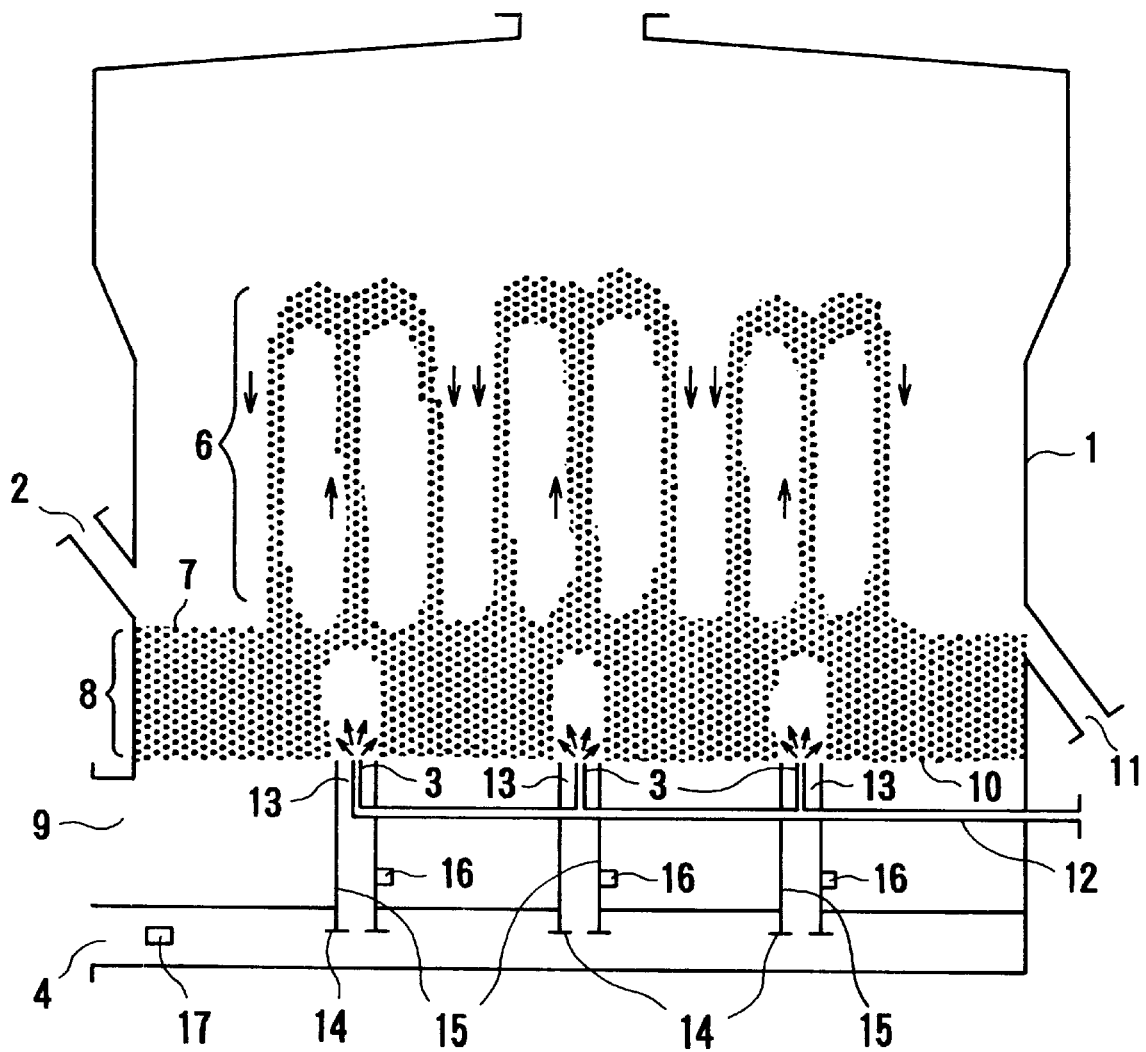

F I G. 2
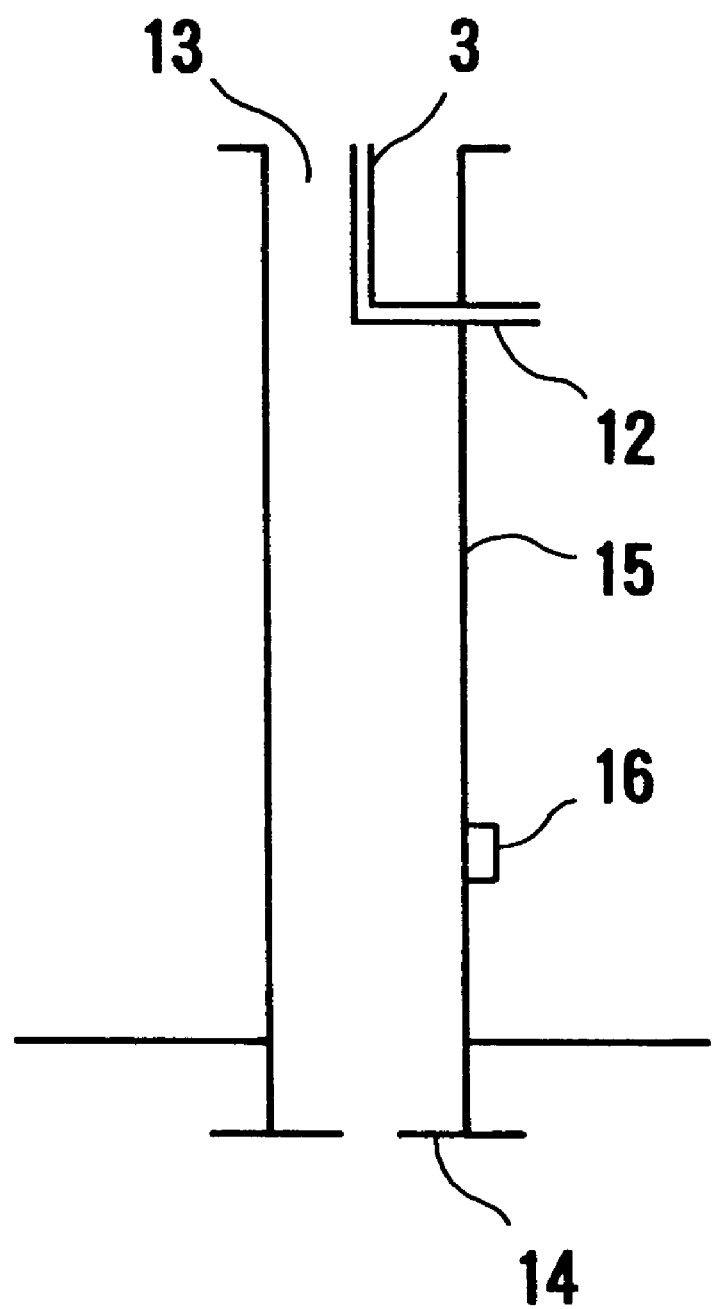

F I G. 3
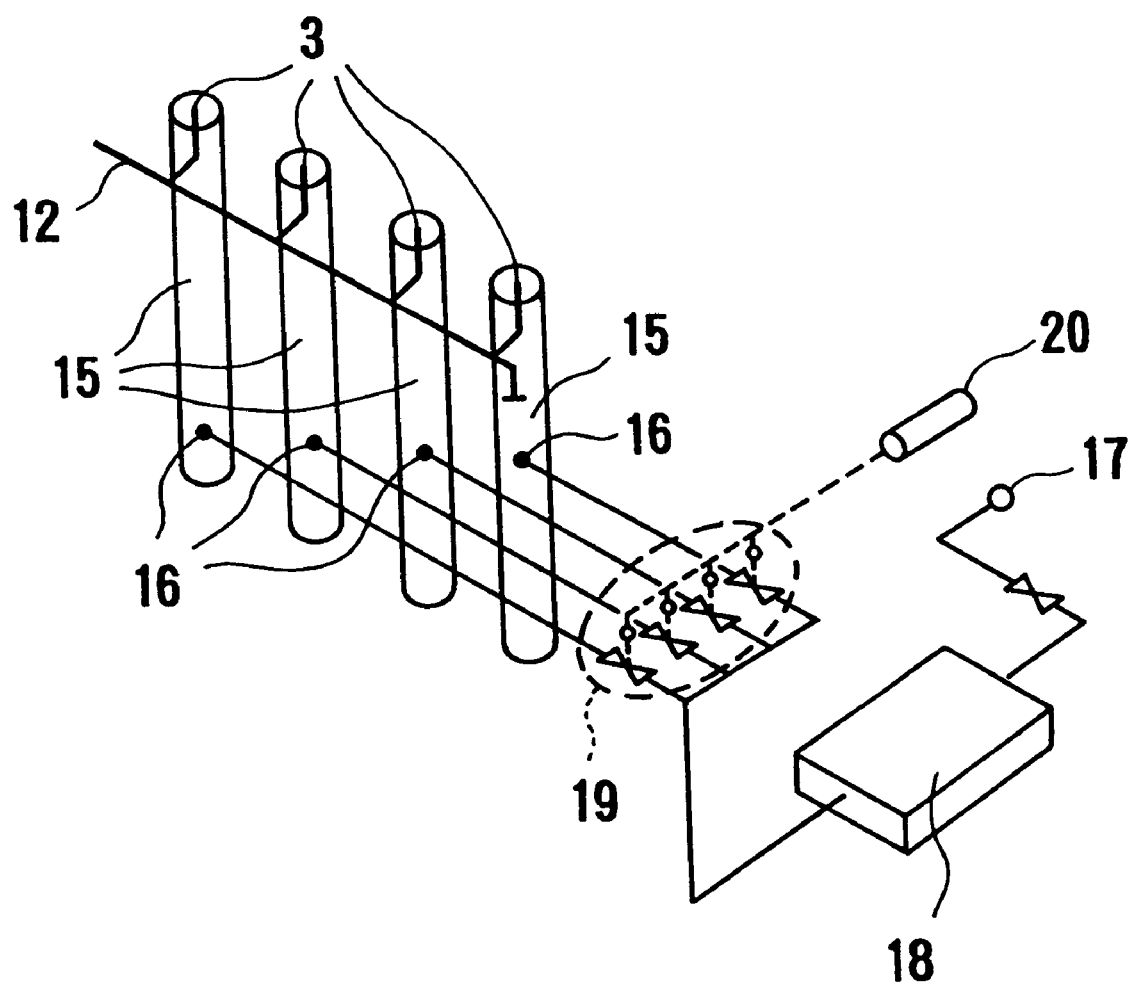

METHOD FOR DETECTING CLOGGING AND GRANULATION METHOD

TECHNICAL FIELD

The present invention relates to a method for detecting clogging in a granulation step of forming granules from a liquid of a molten raw material, such as molten urea. The present invention also relates to a granulation method wherein the feed of a liquid of a raw material to be formed into granules is partially stopped: to a series of sections wherein such clogging has occurred, but the whole apparatus is not stopped, and thereby the method allows continuous operation.

BACKGROUND ART

As the granulation method in a granulation step of forming granules, for example, of urea, and as the method of coating granules, many proposals have been made. For example, the applicant of the present application has proposed a method disclosed in JP-B ("JP-B" means examined Japanese patent publication) No. 63729/1992 as a method for processing large particles of urea. A case of this granulation method is described using a granulator illustrated in FIG. 4, by way of example.

FIG. 4 is a vertical cross-sectional view of a granulator. In this figure, seed crystals of urea are fed into a granulation section 1 through a feed port 2. Molten urea liquid is sprayed at a prescribed angle from nozzles 3 into the granulation section 1. As a result, the above seed crystals of urea are subjected to the spray of molten urea in the granulation section 1 and grow in granule diameter. The grown urea 7 is whirled up into a space 6 by currents for jetting from multiple air feed pipes 5 branched from a lower feed port 4, and the urea 7 is allowed to drop into a space 8. Meanwhile, a fluid for the fluidization is fed from an upper feed port 9, to keep the grown granular urea 7 on a bottom bed 10 in a fluidized state in the space 8, so that the granular urea is fluidized to occupy throughout the space 8 over the nozzles 3. This movement is repeated, and finally the granular urea is discharged from a discharge port 11.

However, in this granulator, sometimes, due to some reason during the continuous operation, the molten urea jetted from the nozzles 3 provided on a line 12, or the grown granular urea 7, adheres to some of outlets 13 of the air feed pipes 5, to prevent the air from being jetted out and to clog the outlets. As a result of the occurrence of the malfunctioned section, the fluidized state in the space 8 becomes turbulent, the granulation

DISCLOSURE OF INVENTION

The present invention has been made with the above circumstances taken into consideration, and the above objects of the present invention have been attained by the following detection method and granulation method.

That is, the present invention provides:

(1) A method for detecting clogging of air feed pipes, comprising air feed pipes, each having an outlet for jetting air into a granulation section, and jetting nozzles, each situated at the center of the air outlet of a said air feed pipe for jetting a liquid of a molten raw material, wherein, in jetting the liquid of the molten raw material from the said jetting nozzles into the granulation section to carry out granulation, (a) an orifice section is provided at a lower part of each of the air feed pipes, a section for taking up orifice rear pressure is provided in each air feed pipe and is located downstream of the orifice section, and a section for taking up orifice forward pressure is provided upstream of the orifice section, and (b) the pressure difference between the said orifice forward pressure and the said orifice rear pressure is measured, to detect clogging of the air feed pipes based on a change (abnormality) in the pressure difference regarding the air feed pipes.

(2) The detection method as stated in the above (1), wherein the liquid of the molten raw material is molten urea.

(3) The detection method as stated in the above (1) or (2), wherein the said air feed pipes are grouped into multiple series of prescribed number of air feed pipes, and the pressure difference of the air feed pipes of each series is monitored.

(4) A granulation method, comprising monitoring a pressure difference by the method as stated in the above (1), (2), or (3) to detect an air feed pipe whose pressure difference is abnormal, stopping the feed of a liquid of a molten raw material to the said air feed pipe, and compensating the amount corresponding to the stoppage with the remaining function.

BRIEF DESCRIPTION OF DRAWINGS

FIG. 1 is a cross-sectional view showing an embodiment of the granulator used in the present invention.

FIG. 2 is an enlarged cross-sectional view of an air feed pipe used in the granulator shown in FIG. 1.

FIG. 3 is an illustrative diagram showing the electrical connection between a differential pressure gauge and sections for taking up pressure of the air feed pipes of FIG. 2.

BEST MODE FOR CARRYING OUT THE INVENTION

Figure 4:
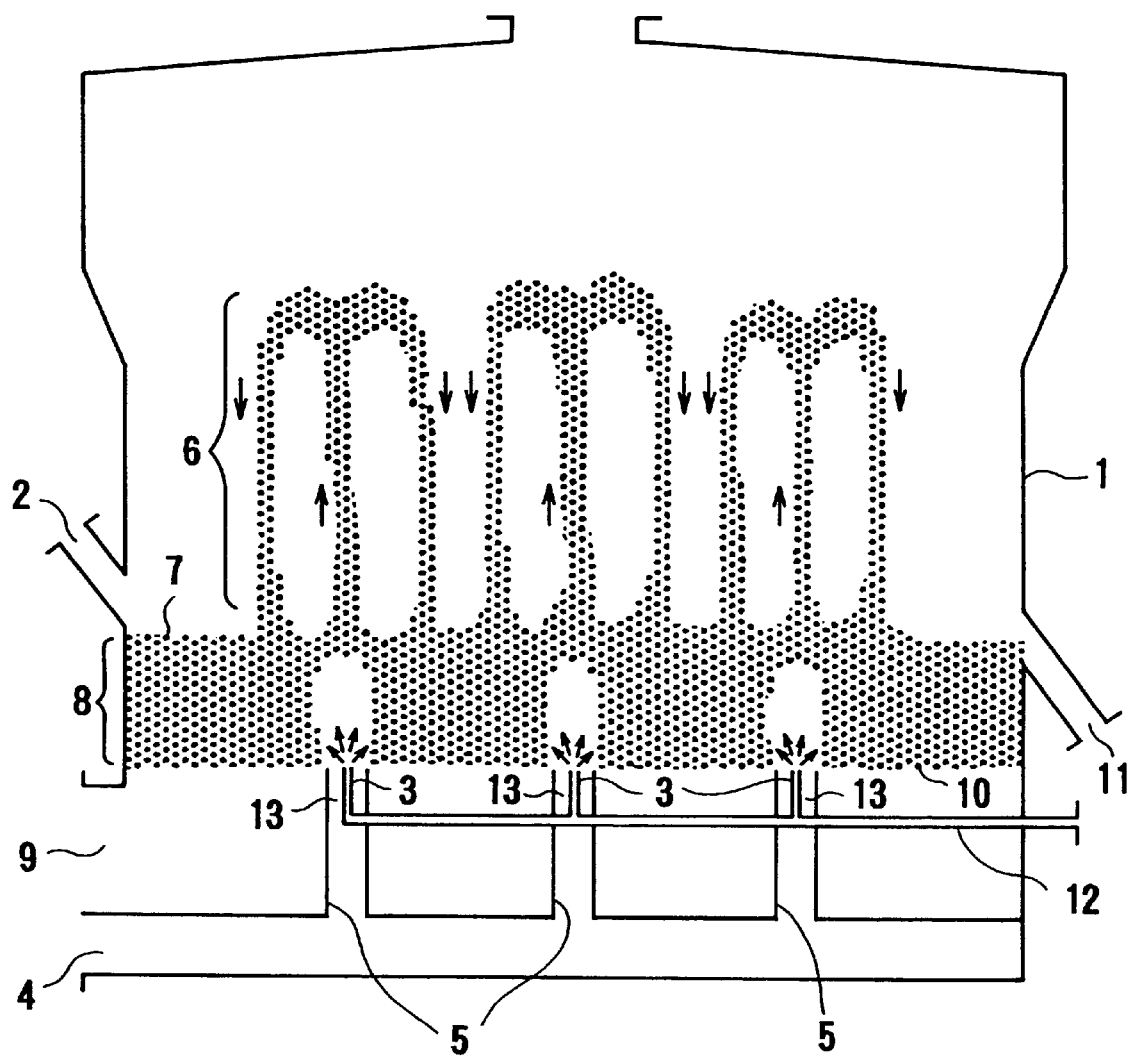
FIG. 4 is a cross-sectional view of an example of a conventional granulator.

A mode of operation of the present invention is explained based on of the embodiments shown in FIGS. 1, 2, and 3; FIG. 1 is a cross-sectional view showing the granulator for use in the present invention; FIG. 2 is an enlarged cross-sectional view of an air feed pipe of the granulator shown in FIG. 1; and FIG. 3 is an illustrative diagram showing the electrical connection between a differential pressure gauge and sections for taking up pressure of the air feed pipes.

As is shown in FIG. 1, the improvement made by the present invention is mainly directed to an air feed system. In the figure, the reference numeral 14 indicates orifices provided at lower parts of air feed pipes 15, the reference numeral 16 indicates sections for taking up orifice rear pressure provided above (downstream of air current) the orifices 14, and the reference numeral 17 indicates a section for taking up orifice forward pressure. The positions of the sections for taking up orifice rear pressure, and of the section for taking up orifice forward pressure, are not particularly restricted, as long as the positions are such that the former sections are desirably located upward away from the orifices by a distance equal to from the diameter (D) of the air feed pipes to 2D, so that a stable pressure may be detected and granules deposited on orifice plates may not be brought into the take-up sections, and as long as the latter section is not just below the orifices. The present invention is characterized by using the air feed pipes 15 having the orifices 14 explained above. In FIG. 1, the same reference numerals in FIG. 4 indicate the same parts.

Referring to FIG. 2, the orifice 14 is provided at a lower part of the air feed pipe 15, the section 16 for taking up orifice rear pressure is provided above the orifice, and the section 17 for taking up orifice forward pressure is provided below the orifice 14. By thus arranging the orifices 14 and allowing a pressure difference to occur, the amounts of air fed into the air feed pipes 15 from a lower feed port 4, shown in FIG. 1, can be equalized.

Although the orifice 14 is provided at a lower end of the air feed pipe 15 in FIG. 2, the present invention is not restricted to that, and the orifice 14 may be located at a point in the air feed pipe 15 above the lower end of the air feed pipe 15.

If the sole object is to cause the pressure difference, instead of the orifices, perforated plates may be adopted. However, use of perforated plates is not desirable because, when a grown body of granules drops from above the air feed pipes 15, shown in FIG. 1, the body of the granules likely becomes a solid or the like, causing clogging.

With respect to the measurement of the pressure differences of the air feed pipes, the pressure differences of the air feed pipes may be monitored individually. Further, as is apparent from the electric connection system diagram in FIG. 3, generally it is desirable that the air feed pipes are grouped into series, with each series consisting of several air feed pipes, and each series is monitored as a group. Although FIG. 3 shows an example in which each series consists of four air feed pipes 15, generally the number of air feed pipes in one series is arbitrarily determined depending on the total number of air feed pipes. Although in FIG. 1 only three air feed pipes are shown, for the purpose of illustration, generally the number of air feed pipes is preferably 100 or less, and the number may be more than that without any particular restrictions.

As is shown in FIG. 3, the pressure difference between the sections 16, for taking up orifice rear pressure, and the section 17, for taking up orifice forward pressure, is measured by a differential pressure gauge 18. Between the differential pressure gauge 18 and the sections 16, for taking up orifice rear pressure, are provided corresponding changeover switches 19, which are switched by a timer 20. The changeover time can be arbitrarily determined, and generally the changeover switches 19 are switched automatically with an interval of 1 to 10 sec.

Generally, in the step of granulating urea, the flow velocity of air flowing through the air feed pipes 15 is about 5 to about 50 m/s, and preferably 10 to 20 m/s. The temperature of the fluid is generally in the range of normal temperatures to 100° C. Further, the flow rate of air is generally in the range of 500 Nm³/H to 3,500 Nm³/H. These conditions are not particularly restricted. The operating conditions of the step of granulating urea can be set in a conventional manner and are disclosed, for example, in JP-B No. 63729/1992.

The pressure difference measured by the differential pressure gauge 18 is sent to a separately provided data collecting apparatus (not shown), and thus the pressure difference is measured in real time, so that the operator, who is an observer, can know the pressure difference of each series all the time. During the operation, if molten urea solidifies and adheres to outlets 13 of the air feed pipes 15, the pressure difference drops. Thus, by observing the decrease in the pressure difference during the operation, clogging of the outlets 13 at the upper parts of the air feed pipes 15 can be detected/predicted. Generally, though the pressure difference during the operation may vary depending on the diameter of the orifices, it is empirically desirable that the pressure difference be set at about 50 mmH$_2$O to 200 mmH$_2$O, which results in particularly no other malfunction due to an increase in pressure difference.

In the case as shown in FIG. 3, wherein the air feed pipes are grouped into series, a decrease in pressure difference in each series can be observed, and a series having a malfunction can be accurately detected. Therefore, by stopping quickly the feed of the raw material liquid (for example, molten urea) to the malfunctioned series, the malfunction can be easily prevented from spreading, allowing continuous operation.

If the feed of the raw material liquid to the malfunctioned series is stopped completely, the amounts of the raw material liquid jetted from the nozzles for jetting the raw material liquid of the remaining series are increased, to allow the output (productivity) to be retained. Although the amount to be increased varies depending, for example, on the number of the air feed pipes and the scale of the granulator, generally it is desirable that, in the case of the granulation of urea, the amount of molten urea to be increased that is jetted from the jetting nozzles is at most about twice.

The method of the present invention is suitable for granulating urea from molten urea as described above. Further, the method of the present invention can be used in the granulation of anything, wherein a liquid of a molten raw material that, when cooled to solidify, will clog the outlets of the air feed pipes in a troublesome way, is to be formed into granules. Further, the granulation includes the case wherein granules are coated.

EXAMPLE

Now, the present invention is described based on examples in more detail. Needless to say, the present invention is not restricted to the following examples.

Example 1

Using a granulator having a basic constitution shown in FIG. 1, urea was granulated. The plant could produce a urea output of 1,000 tons/day. A granulation section 1 had thirty-two air feed pipes 15, each having an orifice 14 and a section 16 for taking up orifice rear pressure, as is shown in FIG. 1, with four air feed pipes 15 constituting one series. The number of lower feed ports 4 shown in FIG. 1 was eight. Therefore, there were No. 1 series to No. 8 series. In each series, the sections 16 for taking up orifice rear pressure of the said air feed pipes were electrically connected to a section for taking up orifice forward pressure as shown in FIG. 3, and the pressure difference between the section 16, for taking up orifice rear pressure, and the section 17, for taking up orifice forward pressure, was measured by a differential pressure gauge 18. A changeover switch 19 between the differential pressure gauge 18 and the sections 16, for taking up orifice rear pressure, was switched by a timer 20. The changeover time was generally at a rate of one change per sec, and the change was carried out automatically. The observed pressure difference was sent to a separately provided data collecting apparatus, and thus the pressure difference was measured in real time.

During the operation, the normal pressure difference of No. 1 series was 100 mmH$_2$O, and 14 days after the start of the operation, the pressure difference was 100 mmH$_2$O, but since the reading of one of the pressure differences in that series indicated 30 mmH$_2$O, the feed of molten urea to that series was stopped automatically. The operation in the steady state was carried out for 30 days. The result of the operation is shown in Table 1.

Comparative Example 1

Continuous operation was carried out in the same manner as in Example 1, except that the power source of the data-collecting apparatus that was used in Example 1 was turned off, so that the differential pressure could not be observed.

After 10 days, since a large mass outside the specification was discharged from the granule discharge port 11, the operation of the granulator was suspended. Thus, within 30 days, it was required to stop the operation from once to three times. The result is shown in Table 1.

Example 2

Since the reading of one of the pressure difference of No. 1 series indicated 30 mmH$_2$O during the operation as shown in Example 1, the feed of molten urea to that series was stopped automatically. After the stoppage, the discharge pressure of the pump was increased, so that the feed of molten urea to the remaining seven series was increased by 8/7-times of the feed to the feed before increasing, to continue the operation. The result is shown in Table 1.

Reference Example 1

Operation was carried out in the same manner as in Comparative Example 1, except that the orifices were removed. The result is shown in Table 1.

TABLE 1

|  | Number of stoppages during 30-day continuous operation |
|---|---|
| Example 1 | 0 |
| Example 2 | 0 |
| Comparative Example 1 | 1 to 3 |
| Reference Example 1 | 5 to 10 |

INDUSTRIAL APPLICABILITY

According to the method of the present invention, a malfunction of a jet of air in the granulation of urea or the like can be detected in an early stage, accurately in real time. Further, according to the method of the present invention, it is not required to stop a plant in order to remove adhered matter, and as a result, since long-term continuous operation becomes possible, the output can be kept constant and a granular product can be supplied stably.

Further, according to the method of the present invention, the occurrence of a malfunction of an air jet section is detected in real time, and in response to the detection an action is taken to prevent the fluid state of floated granules from becoming turbulent, so that the granulator can be operated stably. Therefore, an energy-saved granulation step can be accomplished without consuming excess energy otherwise required for restarting the granulator after stopping the whole granulator completely.

Having described our invention as related to the present embodiments, it is our intention that the invention not be limited by any of the details of the description, unless otherwise specified, but rather be construed broadly within its spirit and scope as set out in the accompanying claims.

We claim:

1. A method for detecting clogging of air feed pipes, comprising air feed pipes, each having an outlet for jetting air into a granulation section, and jetting nozzles, each situated at the center of the air outlet of a said air feed pipe for jetting a liquid of a molten raw material, wherein, in jetting the liquid of the molten raw material from the said jetting nozzles into the granulation section to carry out granulation, (a) an orifice section is provided at a lower part of each of the air feed pipes, a section for taking up orifice rear pressure is provided in each air feed pipe and is located downstream of the orifice section, and a section for taking up orifice forward pressure is provided upstream of the orifice section, and (b) the pressure difference between the said orifice forward pressure and the said orifice rear pressure is measured, to detect clogging of the air feed pipes based on a change (abnormality) in the pressure difference regarding the air feed pipes.

2. The detection method as claimed in claim 1, wherein the liquid of the molten raw material is molten urea.

3. The detection method as claimed in claim 1, wherein the said air feed pipes are grouped into multiple series of prescribed number of air feed pipes, and the pressure difference of the air feed pipes of each series is monitored.

4. A granulation method, comprising monitoring a pressure difference by the method according to claim 1, to detect an air feed pipe whose pressure difference is abnormal, stopping the feed of a liquid of a molten raw material to the said air feed pipe, and compensating the amount corresponding to the stoppage with the remaining function.

5. The granulation method as claimed in claim 4, wherein the liquid of the molten raw material is molten urea.

6. The granulation method as claimed in claim 4, wherein the said air feed pipes are grouped into multiple series of prescribed number of air feed pipes, and the pressure difference of the air feed pipes of each series is monitored.

7. The granulation method as claimed in claim 4, wherein by stopping the feed of the liquid of the molten raw material to the air feed pipe whose pressure difference is abnormal, clogging is prevented from spreading to other air feed pipes, to allow continuous operation.

8. The granulation method as claimed in claim 4, wherein the feed of the liquid of the molten raw material to the air feed pipe whose pressure difference is abnormal is stopped, and the amounts of the liquid of the molten raw material that is jetted from the jetting nozzles for jetting the liquid of the molten raw material in air feed pipes whose pressure difference is normal, are increased.

\* \* \* \* \*